(12) United States Patent
Yakhini et al.

(10) Patent No.: US 7,371,580 B2
(45) Date of Patent: May 13, 2008

(54) USE OF UNSTRUCTURED NUCLEIC ACIDS IN ASSAYING NUCLEIC ACID MOLECULES

(75) Inventors: Zohar H. Yakhini, Ya'acov (IL); Jeffrey R Sampson, Burlingame, CA (US); Joel Myerson, Berkeley, CA (US)

(73) Assignee: Agilent Technologies, Inc., Santa Clara, CA (US)

( * ) Notice: Subject to any disclaimer, the term of this patent is extended or adjusted under 35 U.S.C. 154(b) by 450 days.

(21) Appl. No.: 09/938,937

(22) Filed: Aug. 24, 2001

(65) Prior Publication Data

US 2003/0211474 A1    Nov. 13, 2003

(51) Int. Cl.
*G01N 33/00* (2006.01)
*C12Q 1/68* (2006.01)
*C12M 1/36* (2006.01)

(52) U.S. Cl. .................. 436/94; 435/6; 435/287.2; 536/23.1; 536/24.3; 436/800

(58) Field of Classification Search .............. 435/6, 435/91.1, 91.2, 287, 2; 436/94; 536/23.1, 536/24.3
See application file for complete search history.

(56) References Cited

U.S. PATENT DOCUMENTS

| | | | | |
|---|---|---|---|---|
| 5,200,313 A | * | 4/1993 | Carrico | 435/6 |
| 6,077,674 A | * | 6/2000 | Schleifer et al. | 435/6 |
| 6,428,957 B1 | * | 8/2002 | Delenstarr | 435/6 |
| 7,052,841 B2 | | 5/2006 | Delenstarr | |
| 2006/0246494 A1 | | 11/2006 | Delenstarr | |

FOREIGN PATENT DOCUMENTS

EP         1 072679 A      1/2001

OTHER PUBLICATIONS

A. Ben-Dor, et al., "Universal DNA Tag Systems: A Combinatorial Design Scheme"; Journal of Computational Biology, vo. 7, No. 3/4, 2000, pp. 403-519.
D. G. Wang, et al., "Large-Scale Identification, Mapping, and Genotyping of Single-Nucleotide Polymorphisms in the Human Genome"; American Association for the Advancement of Science, US vol. 280, 1998, pp. 1077-1082.
M. Chee, et al., "Accessing Genetic Information with High-Density DNA ARrays", American Association for the Advancement of Science, US, vol. 274, Oct. 25, 1999, pp. 610-614.
Blanchard and Hood. *Nature Biotechnology.* 14:1649, 1996.
Chee, M. et al., (1996) *Science* 274:610-614.
DeRisi et al., *Science.* 278:680-686, 1997.
Pease et al., *Proc. Natl. Acad. Sci. USA* 91:5022-5026, 1994.

* cited by examiner

*Primary Examiner*—Bradley L. Sisson

(57) ABSTRACT

The present invention provides a system and methods for assaying nucleic acid molecules with reduced levels of background signal and enhanced specificity and sensitivity. In particular, the present invention provides a system and methods for detecting, sorting, tracking and characterizing nucleic acid molecules using hybridization assays with reduced levels of undesirable cross hybridization and reduced levels of intramolecular secondary structure.

5 Claims, 9 Drawing Sheets

Figure 3
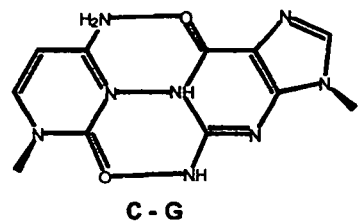
C - G
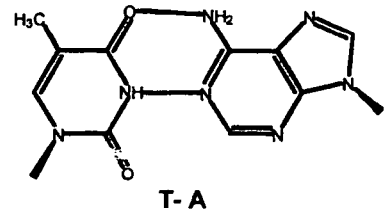
T - A
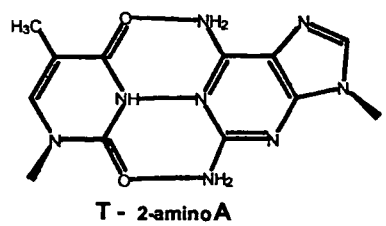
T - 2-aminoA
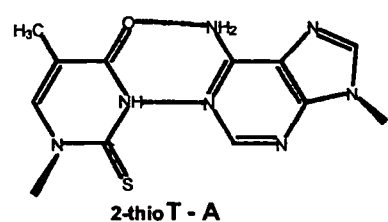
2-thioT - A
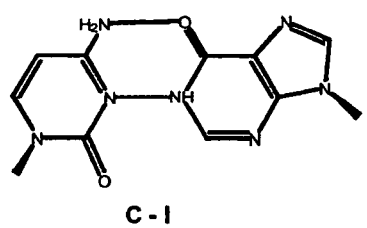
C - I
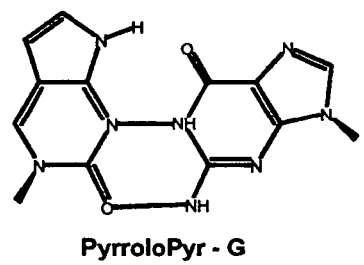
PyrroloPyr - G
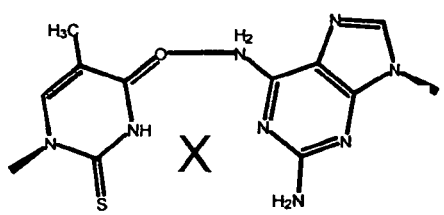
2-thioT - 2-aminoA
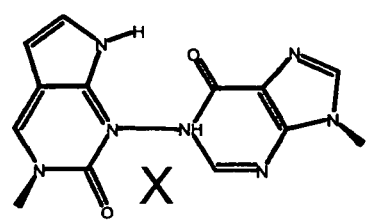
PyrroloPyr - I
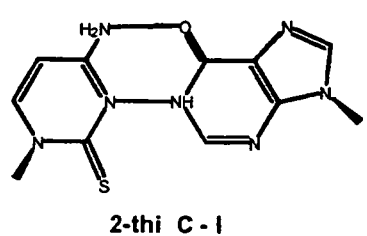
2-thi C - I
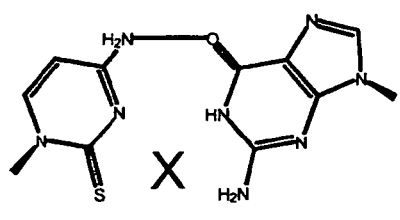
2-thi C - G

A

5'-CGATAGGCTCTG →
3'-GCTATCCGAGACCCTGACTTGACACCTGTT-5'

B

Figure 5
A
```
               GACTGA →
3'-GCTATCCGAGACACTGACTTGACACCTGTT-5'
```
B
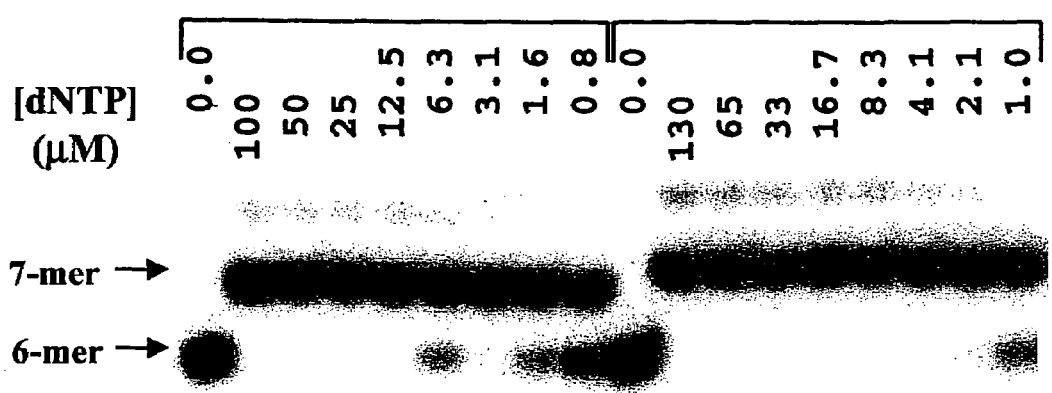
C
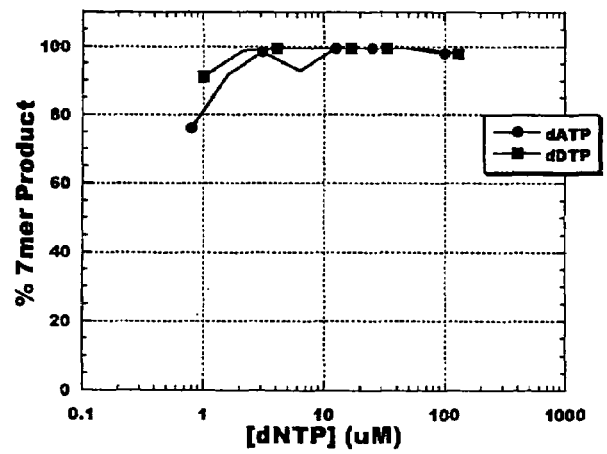

Figure 6
A
B
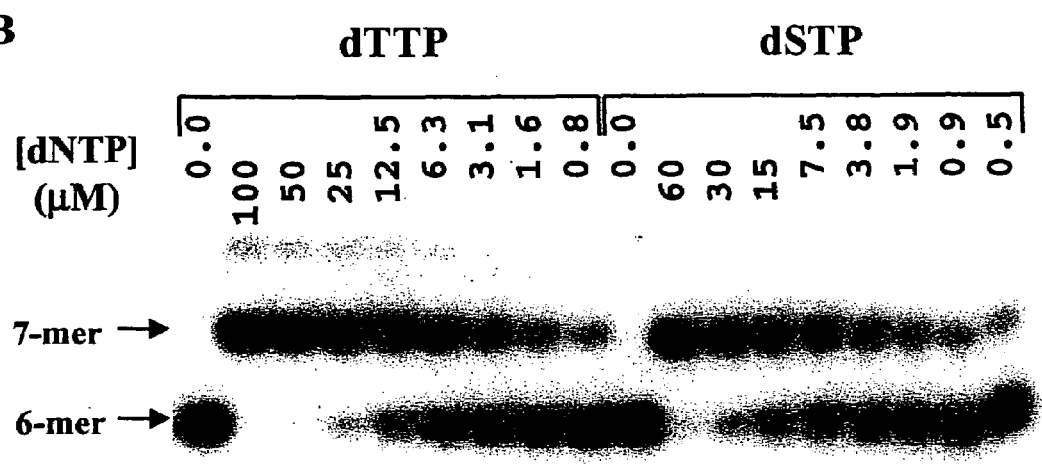
C
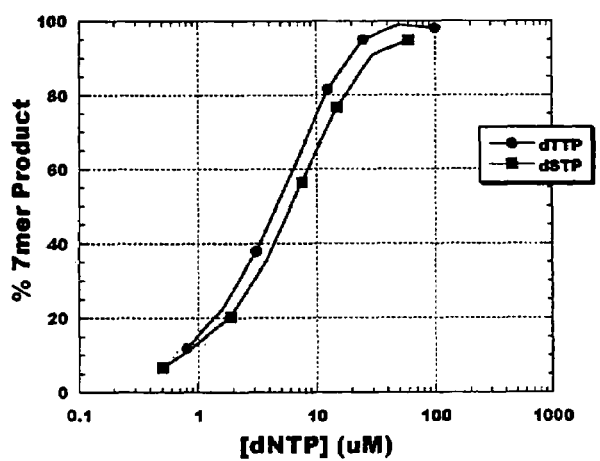

Figure 7
A
B
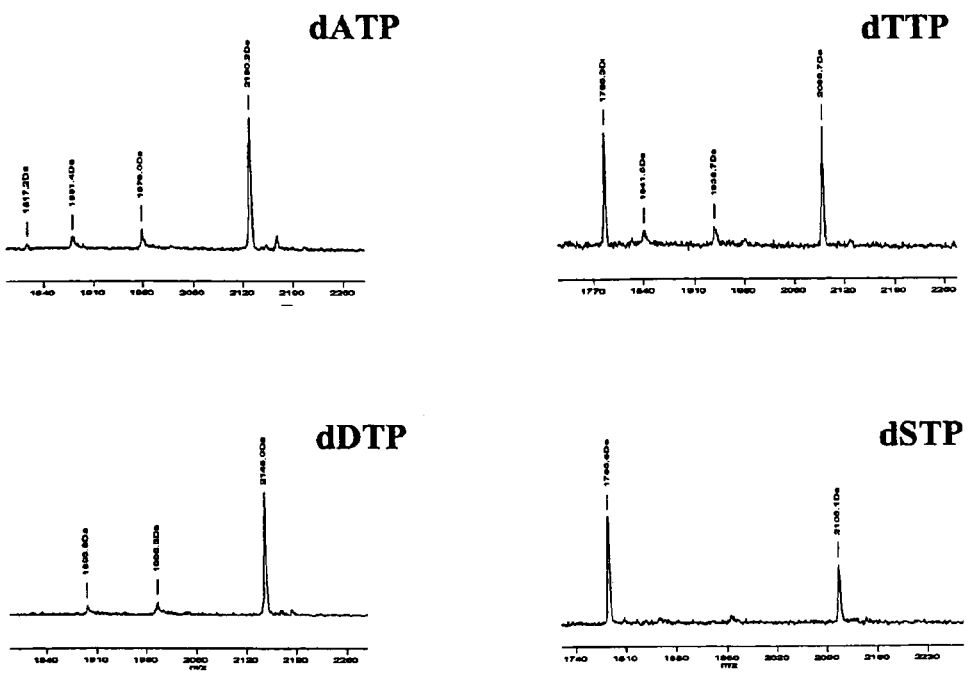
C
| Extension Nucleotide | X-mer | Predicted m/z (Positive Ion)* | Measured m/z (Positive Ion) | Predicted Δ m/z | Measured Δ m/z |
|---|---|---|---|---|---|
| None | GACTGA | 1816.3 | nd | -- | -- |
| dATP | GACTGAA | 2129.5 | 2130.2 | -- | -- |
| dDTP | GACTGAD | 2144.5 | 2146.0 | +15.0 | +15.8 |
| None | GCTCTG | 1783.2 | 1785.4 + 0.2 | -- | -- |
| dTTP | GCTCTGT | 2087.4 | 2089.7 | -- | -- |
| dSTP | GCTCTGS | 2103.4 | 2106.1 | +16.0 | +16.4 |

Figure 8

```
5'-CTATCCGATCCATC→
3'-GATAGGCTAGGTAGTTCAAGTCAGAGCTTTGTCAGAGTTGTAAACAGGTGTCGCATp-5'
```

↓ dNTPs
  Bst DNA Polymerase

```
5'-CTATCCGATCCATCaagttcagtctcgaaacagtctcaacatttgtccacagcgta
3'-GATAGGCTAGGTAGTTCAAGTCAGAGCTTTGTCAGAGTTGTAAACAGGTGTCGCAT
                                                          ←
```

↓ λ Exonuclease

```
5'-CTATCCGATCCATCaagttcagtctcgaaacagtctcaacatttgtccacagcgta-3'
```

USE OF UNSTRUCTURED NUCLEIC ACIDS IN ASSAYING NUCLEIC ACID MOLECULES

FIELD

The present invention is in the area of nucleic acids analysis and nucleic acid biochemistry, and relates to analytical tools and methods for assaying gene expression and mutations in gene sequences. In particular, the invention relates to assay systems, tools and methods for enhanced specificity and sensitivity for assaying multiple samples simultaneously. More specifically, the invention addresses methods for reducing cross hybridization between target and probe molecules when employing universal addressable array, bead or tag methods.

BACKGROUND

Numerous analytical methods in molecular biology, biochemistry and biophysics rely on the hybridization of a nucleic acid molecule to a complementary nucleic acid molecule. These methods include Southern and Northern blot hybridization, fluorescence in situ hybridization (FISH), gene-chip array technologies, and polymerase chain reactions (PCR). One goal of these methods is to determine the presence and/or amounts of nucleic acid molecules containing a particular nucleotide sequence(s) of interest. In general, nucleic acid molecules are labeled with a detectable marker such as a radioactive or a fluorescent marker. After sequence-specific hybridization of two nucleic acid molecules, the presence and/or level is measured using the marker.

The development of DNA "chips" which are arrays of nucleic acid molecules on a solid support such as a glass surface, has greatly increased the number of nucleotide sequences that can be assayed simultaneously within a given sample (Chee, M., et al., (1996) *Science* 274, 610-614). In particular, array-based hybridization assays can simultaneously monitoring of thousands of hybridization reactions from one sample allowing researchers to obtain information on the presence and quantities of numerous nucleic acids having numerous sequences of interest (Solas et al. *Proc. Natl. Acad. Sci. USA* 91:5022-5026, 1994; Blanchard and Hood. *Nature Biotechnology.* 14:1649, 1996; and DeRisi et al. *Science.* 278:680-686, 1997). These assays may be applied to a wide range of applications such as single-nucleotide polymorphism (SNP) genotyping, gene expression profiling, and resequencing DNA.

A typical DNA array consists of a set of oligonucleotides bound to a solid support surface such as silicon or glass. A fluorescently labeled target sample mixture of DNA or RNA fragments is brought in contact with the array and allowed to hybridize with the synthesized oligonucleotides. In theory, the conditions only allow hybridization between a region of a target molecule and a complementary oligonucleotide on the surface. Therefore, detecting areas of fluorescence on the surface provides information about the nucleic acid content in the sample. However in practice, cross-hybridization is a significant source of error in a standard array-based hybridization assay, and reduces the sensitivity and selectivity of the assay and/or introduces background signals.

In general, cross-hybridization is the undesired binding of two or more nucleic acid molecules, and depends on the specific protocol of the method employed. For DNA array based assays, one form of cross hybridization which produces experimental error and limits the power of the assay, occurs when regions of target nucleic acids in a sample hybridize to an improper site on the DNA array. Such cross hybridization may result in false positive and negative signals in the assay. Additional cross hybridization occurs when nucleic acid molecules in a sample (target) hybridize to themselves or to other nucleic acid molecules in the sample.

The control of cross-hybridization is particularly important for methods that employ massively parallel arrays of hybridization probes such as for DNA chips. Such arrays depend solely upon hybridization for specificity since there is no enzyme-based proofreading of duplexes as in methods based upon Sanger dideoxy sequencing or the polymerase chain reaction. In addition, the large number of probes reduces the ability to verify the specificity of all probe-target interactions that are detected in a given assay. Thus, the accuracy of data obtained using DNA microarrays is greatly improved by minimizing cross-hybridization. Therefore, a particularly problematic form of cross-hybridization occurs in DNA gene chip technology when a nucleic acid in a sample hybridizes to the wrong probe on the DNA chip.

Fragmentation of the target reduces cross hybridization to some degree since shorter targets offer fewer secondary sites for binding by another target molecule. However, fragmentation also decreases signal for detection of target molecules (e.g. if the target has been randomly labeled with a reporter molecule), and increases the complexity of sample preparation protocols. Fragmentation is particularly problematic in differential expression studies where two samples labeled with different reporter molecules must be reproducibly and identically fragmented.

Therefore, there is a need for methods of analyzing nucleic acid molecules that reduce undesired hybridization between two or more nucleic acid molecules.

SUMMARY OF THE INVENTION

The present invention provides a system and methods for assaying nucleic acid molecules with reduced levels of background signal and enhanced specificity and sensitivity. In particular, the present invention provides a system and methods for detecting, sorting, tracking and characterizing nucleic acid molecules using hybridization assays with reduced levels of undesirable cross hybridization and reduced levels of intramolecular secondary structure.

In one aspect of the present invention, a system is provided for assaying target nucleic acid molecules with reduced background signal and enhanced sensitivity. The system of the present invention minimizes undesired cross hybridization in universal nucleic acid array-based assays between anti-target sequences and anti-tag sequences. The system comprises a first plurality of nucleic acid probes called anti-tags comprising unstructured nucleotides which have a reduced ability to hybridize to other complementary nucleic acids containing unstructured nucleotides. Additionally, unstructured nucleic acids have the ability to hybridize to nucleic acids containing natural nucleotides and modified nucleotides that are not unstructured. Anti-tags may be in solution or immobilized on a solid support. Preferably, the anti-tag molecules immobilized on a solid support. However, any method of identifying anti-tag molecules in solution or attached to a solid support such that anti-tag molecules having different nucleotide sequences are differentiated may be used in accordance with the present invention.

The system further comprises a second plurality of nucleic acid molecules, called intermediary nucleic acid molecules, comprising a first and a second region (see FIG. 1). The first region of the intermediary nucleic acid molecule is designed to be complementary to and also hybridize to an anti-tag molecule, and is referred to herein as the "tag" sequence. Preferably, each first region of each intermediary molecule (tag) that has a different sequence hybridizes to a different anti-tag molecule. Methods of designing tag/anti-tag sequences to provide a method of sorting nucleic acids are known in the art (see for example Ben-Dor et al. (*J. of Comp. Biol.* 7(3-4):503-519, 2000 and references cited therein.)

Additionally, the intermediary nucleic acids comprise a second region which is referred to herein as the "anti-target" regions. The second "anti-target" region of the intermediary molecule comprises unstructured nucleotides that minimize or eliminate undesired cross hybridization between anti-target and anti-tag sequences that also comprise unstructured nucleic acids. The second "anti-target" region of the intermediary molecule comprising unstructured nucleotides is designed to be complementary to a potential target nucleic acid molecule of interest in a sample. The unstructured nucleotides of the second "anti-target" region hybridize to complementary target molecules.

The set of tag molecules sorts and assembles the target nucleic acids onto the anti-tag molecules which are labeled, ordered or spatially array in a manner that allows one of ordinary skill to retrieve information about the sequence of the anti-tag molecule. The hybridization between the target/anti-target and between the tag/anti-tag may be performed simultaneously or preferably, in two hybridization steps (Ben-Dor et al. supra).

The anti-tag molecules and anti-target molecules each comprise unstructured nucleotides (UNAs) such that anti-target and anti-tag molecules have a reduced ability to hybridize to each other and to themselves as compared to nucleic acids molecules with naturally occurring nucleotides (FIG. 2). The molecules containing unstructured nucleotides do not have a reduced ability to hybridize to other nucleic acid molecules having non-modified nucleotides or nucleotides structurally modified in a manner that does not reduce the ability of the nucleotide to hybridize to a complement. The present invention therefore reduces the cross-hybridization between potentially complementary anti-tag and anti-target nucleic acid molecules (FIG. 1B). This form of cross-hybridization leads to false signals and reduces the amount of available tag molecules in the assay for proper target detection and identification.

Each set of anti-tag/tag sequences is generic to the biological sample to be tested. Preferably, each intermediary nucleic acid contains a uniquely paired tag and anti-target sequences. However, it is within the scope of the present invention to have multiple anti-target sequences pair with one tag sequence. Furthermore, it is also within the scope of the present invention to have multiple tag sequences paired with one anti-target sequence.

In another aspect of the present invention, a method of assaying nucleic acid molecules with reduced background signal and increased sensitivity and specificity is provided.

In yet another aspect of the present invention, a kit for assaying nucleic acid molecules with reduced background signal and increases sensitivity and specificity is provided.

BRIEF DESCRIPTION OF THE DRAWINGS

FIG. 3 is a schematic representation of base-paring schemes for the two natural and modified nucleotide pairs. The bold X indicates the disruption of the natural hydrogen-bonding interaction.

FIG. 4B is a phosphorimage of the 10% denaturing PAGE analysis of the polymerase extension reactions. The dNTP composition (A (or D), G, C & T (or S)) and polymerase present in each reaction are indicated. The $^{32}$P-labeld primer and 30-mer products are indicated by arrows.

FIG. 5A shows the 6-mer/template sequence used to test the incorporation of the 2-amino-2'-deoxyadenosine triphosphate in a polymerase extension reaction.

FIG. 5B is a phosphorimage of the 20% denaturing PAGE analysis of the polymerase extension reactions. The dATP and dDTP concentration present in each reaction are indicated. The $^{32}$P-labeld 6-mer and 7-mer product are indicated by arrows. FIG. 5C is a graphic representation of the % 7-mer product vs dNTP concentration.

FIG. 6A shows a 6-mer/template sequence used to test the incorporation of the 2-thiothymidine triphosphate in a polymerase extension reaction. FIG. 6B is a phosphorimage of the 20% PAGE analysis of the polymerase extension reactions. The dTTP and 2-thioTTP concentration present in each reaction are indicated. The $^{32}$P-labeld 6-mer and 7-mer product are indicated by arrows. FIG. 6C is a graphic representation of the % 7-mer product vs dNTP concentration.

FIG. 7A shows the 6-mer/template sequences used to test the incorporation of the 2-amino-2'-deoxyadenosine and 2-thiothymidine triphosphate in the polymerase extension reaction. FIG. 7B is a MALDI mass spectra of the polymerase extension reactions containing the indicated dNTP. Then m/z values for the 6-mer and 7-mer extension products are indicated. FIG. 7C is a summary of the predicted and measured m/z values for the 6-mer and 7-mer extension products.

FIG. 8 depicts a scheme for generating single-stranded polynucleotides using a primer-template dependent polymerase extension reaction followed by digestion of the template DNA with λ exonuclease.

DEFINITIONS

Figure 1A:
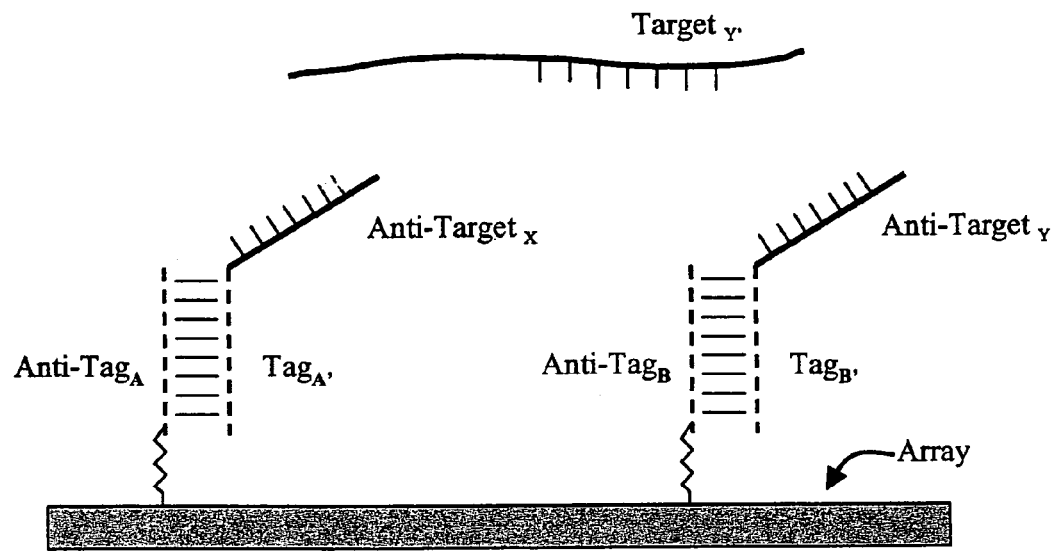
FIG. 1 is a schematic representation of an array-based Tag/AntiTag method for addressing Target sequences to defined features on an array. The $Tag_A$ region of the intermediate molecule is designed to hybridize to the $Anti-Tag_A$ oligonucleotide on the array while the $Anti-Target_X$ region of the intermediate molecule is designed to hybridize to the Target molecule. By analogy, the $Tag_B$ region of the intermediate molecule is designed to hybridize to the $Anti-Tag_B$ oligonucleotide on the array while the $Anti-Target_Y$ region of the intermediate molecule is designed to hybridize to the Target molecule.
FIG. 1B is a schematic representation of potential mis-hybridization between the $Anti-Tag_A$ oligonucleotide on the array and the $Anti-Target_X$ region of the intermediate molecule.

"Polynucleotide": A polynucleotide as used herein means a compound or composition that is a polymeric nucleotide or nucleic acid polymer. The polynucleotide may be a natural compound or a synthetic compound. In the context of an assay, the polynucleotide can have from about 5 to 5,000,000 or more nucleotides. The larger polynucleotides are generally found in the natural state. In an isolated state the polynucleotide can have about 30 to 50,000 or more nucleotides, usually about 100 to 20,000 nucleotides, more frequently 500 to 10,000 nucleotides. Isolation of a polynucleotide from the natural state often results in fragmentation. The polynucleotides include nucleic acids, and fragments thereof, from any source in purified or unpurified form including DNA, double-stranded or single stranded (dsDNA and ssDNA), and RNA, including transfer RNA, messenger RNA, ribosomal RNA, mitochondrial DNA and RNA, chloroplast DNA and RNA, DNA/RNA hybrids, or mixtures thereof, genes, chromosomes, plasmids, the genomes of biological materials such as microorganisms, e.g. bacteria, yeasts, viruses, viroids, molds, fungi, plants, animals, humans, and the like. The polynucleotide can be only a minor fraction of a complex mixture such as a biological sample. Polynucleotides also include genes.

Polynucleotides include analogs of naturally occurring polynucleotides in which one or more nucleotides are modified over naturally occurring nucleotides. Polynucleotides then, include compounds produced synthetically (for example, peptide nucleic acids "PNA" as described in U.S. Pat. No. 5,948,902 and the references cited therein) which can hybridize in a sequence specific manner analogous to that of two naturally occurring polynucleotides.

In addition, polynucleotides include modifications of the phosphodiester backbone. For example, phosphorothioate-modified backbones have been used to increase the stability of nucleic acids by altering the susceptibility of the modified backbone to nuclease cleavage (Agrawal. *Biochim Biophys Acta* 1489(1):53-68. 1999; Zon et al. *Anticancer Drug Des* 6(6):539-68, 1991).

The polynucleotide can be obtained from various biological materials by procedures well known in the art. The polynucleotide, where appropriate, may be cleaved to obtain a fragment that contains a target nucleotide sequence, for example, by shearing or by treatment with a restriction endonuclease or other site specific chemical cleavage method, such as limited RNase digestion, to produce smaller RNA fragments.

For purposes of this invention, the polynucleotide, or a cleaved fragment obtained from the polynucleotide, will usually be at least partially denatured or single stranded or treated to render it denatured or single stranded. Such treatments are well known in the art and include, for instance, heat and/or alkali treatment, or enzymatic digestion of one strand. For example, double stranded DNA (dsDNA) can be heated at 90-100° C. for a period of about 1 to 10 minutes to produce denatured material, while RNA produced via transcription from a dsDNA template is already single stranded.

"Oligonucleotide": An oligonucleotide as used herein means a polynucleotide, usually single stranded, usually a synthetic polynucleotide but may be a naturally occurring polynucleotide. The oligonucleotide(s) are usually comprised of a sequence of at least 5 nucleotides, usually, 10 to 100 nucleotides, more usually, 20 to 50 nucleotides, preferably, 10 to 30 nucleotides, more preferably, 20 to 30 nucleotides, and desirably about 25 nucleotides in length. For the purposes of the invention, the term "oligonucleotide" includes the term "polynucleotide", unless stated otherwise.

"Oligonucleotide probe": An oligonucleotide probe as used herein is an oligonucleotide employed to bind to another oligonucleotide.

"Nucleotide": A nucleotide as used herein means to the monomeric unit of nucleic acid polymers, i.e., DNA and RNA, whether obtained from a natural source or produced synthetically, which comprises a nitrogenous heterocyclic base, which is a derivative of either a purine or pyrimidine, a pentose sugar, and a phosphate (or phosphoric acid). When the phosphate is removed, the monomeric unit that remains is a "nucleoside". Thus a nucleotide is a 5'-phosphate of the corresponding nucleoside. For the purposes of the invention, "nucleotide" includes its corresponding nucleoside and phosphodiester, and "oligonucleotide" includes its corresponding oligonucleoside and oligophosphodiester, unless indicated otherwise.

"Unstructured nucleic acid (UNA)": An unstructured nucleic acid as used herein refers to a nucleic acid molecule having one or both members of a nucleotide base pair wherein one or both members of the base pair comprises a modified base and/or modified sugar such that the base pair has a reduced ability to form a stable hydrogen-bonded base pair. The reduction in the ability to form hydrogen bonded base pairs is compared to the number of hydrogen bonds in a base pair comprising non-modified bases. An adenine-thymine base pair (or adenine-uracil for RNA) has two hydrogen bonds, and a guanine-cytosine base pair has three hydrogen bonds. "Unstructured nucleic acids" also includes in its definition, a nucleic acid molecule comprising a modified nucleotide bases or sugars in accordance with the above definition, wherein the modified nucleotide forms a stable base pair with another complementary nucleotide.

An oligonucleotide or a polynucleotide comprising unstructured nucleotides has a reduced ability to hybridize to other oligonucleotides or polynucleotides having regions of complementarity comprising complementary unstructured nucleotides. The reduction in level of hybridization between two molecules is compared to two nucleic acid molecules having the same nucleotide sequences with non-modified nucleotides or with nucleotides modified in a manner that does not reduce the number of hydrogen bonds in the base pair.

"Hybridization": Hybridization as used in the context of nucleotide sequences means to the ability of two nucleotide sequences to hybridize with each other and is based in part on the degree of complementarity of the two nucleotide sequences, which in turn is based on the fraction of matched complementary nucleotide pairs. The more nucleotides in a given sequence that are complementary to another sequence, the more stringent the conditions can be for hybridization and the more specific will be the binding of the two sequences. Increased stringency is achieved by elevating the temperature, increasing the ratio of co-solvents, lowering the salt concentration, and the like. In the context of ligand/receptor, antibody/antigen, etc., binding depends on the affinity each of the specific binding pair for the other and means a relatively stable bond between respective pairs.

"Complementary": Complementary bases are defined according to the Watson-Crick definition for base pairing. Adenine base is complementary to thymine base and forms a stable base pair. Guanine base is complementary to cytosine base and forms a stable base pair. Complementation of modified base analogs is defined according to the parent nucleotide. Complementation of modified bases does not require the ability to form stable hydrogen bonded base pairs. In other words, two modified bases may be complementary according to identity of the modified base but may not form a stable base pair. Complementation of base analogs which are not considered derivatives of A, T, G, C or U is defined according to an ability to form a stable base pair with a base or base analog. For example, a particular derivative of C (i.e. 2-thiocytosine) may not form a stable base pair with G, but is still considered complementary.

In addition to purines and pyrimidines, modified bases or analogs, as those terms are used herein, include any compound that can form a hydrogen bond with one or more naturally occurring bases or with another base analog. Any compound that forms at least two hydrogen bonds with T (or U) or with a derivative of T or U is considered to be an analog of A or a modified A. Similarly, any compound that forms at least two hydrogen bonds with A or with a derivative of A is considered to be an analog of T (or U) or a modified T or U. Similarly, any compound that forms at least two hydrogen bonds with G or with a derivative of G is considered to be an analog of C or a modified C. Similarly, any compound that forms at least two hydrogen bonds with C or with a derivative of C is considered to be an analog of G or a modified G. It is recognized that under this scheme, some compounds will be considered for example to be both A analogs and G analogs (purine analogs) or both T/U analogs and C analogs (pyrimidine analogs).

"Substrate or surface": A substrate or surface as used herein means to a porous or non-porous water insoluble material. The surface can have any one of a number of shapes, such as strip, plate, disk, rod, particle, including bead, and the like. The substrate can be hydrophobic or hydrophilic or capable of being rendered hydrophobic or hydrophilic and includes inorganic powders such as silica, magnesium sulfate, and alumina; natural polymeric materials, particularly cellulosic materials and materials derived from cellulose, such as fiber containing papers, e.g., filter paper, chromatographic paper, etc.; synthetic or modified naturally occurring polymers, such as nitrocellulose, cellulose acetate, poly (vinyl chloride), polyacrylamide, cross linked dextran, agarose, polyacrylate, polyethylene, polypropylene, poly (4-methylbutene), polystyrene, polymethacrylate, poly(ethylene terephthalate), nylon, poly(vinyl butyrate), etc.; either used by themselves or in conjunction with other materials; glass available as Bioglass, ceramics, metals, and the like. Natural or synthetic assemblies such as liposomes, phospholipid vesicles, and cells can also be employed. Common substrates used for arrays are surface-derivatized glass or silica, or polymer membrane surfaces, as described in Z. Guo et al. (*Nucleic Acids Res* 22, 5456-65, 1994) and U. Maskos, E. M. Southern, *Nucleic Acids Res* 20, 1679-84 (1992) and E. M. Southern et al., *Nucleic Acids Res* 22, 1368-73 (1994), both incorporated herein by reference.

Immobilization of oligonucleotides on a substrate or surface may be accomplished by well-known techniques, commonly available in the literature. See, for example, A. C. Pease, et al., *Proc. Nat Acad. Sci. USA,* 91:5022-5026 (1994); Z. Guo, R. A. Guilfoyle, A. J. Thiel, R. Wang, L. M. Smith, *Nucleic Acids Res* 22, 5456-65 (1994); and M. Schena, D. Shalon, R. W. Davis, P. O. Brown, *Science,* 270,467-70(1995).

"Label": A label as used herein means to a member of a signal producing system. Usually the label is part of a target nucleotide sequence or an oligonucleotide probe, either being conjugated thereto or otherwise bound thereto or associated therewith. The label is capable of being detected directly or indirectly. Labels include (i) reporter molecules that can be detected directly by virtue of generating a signal, (ii) specific binding pair members that may be detected indirectly by subsequent binding to a cognate that contains a reporter molecule, (iii) oligonucleotide primers that can provide a template for amplification or ligation or (iv) a specific polynucleotide sequence or recognition sequence that can act as a ligand such as for a repressor protein, wherein in the latter two instances the oligonucleotide primer or repressor protein will have, or be capable of having, a reporter molecule. In general, any reporter molecule that is detectable can be used.

The reporter molecule can be isotopic or nonisotopic, usually nonisotopic, and can be a catalyst, such as an enzyme, a polynucleotide coding for a catalyst, promoter, dye, fluorescent molecule, chemiluminescer, coenzyme, enzyme substrate, radioactive group, a small organic molecule, amplifiable polynucleotide sequence, a particle such as latex or carbon particle, metal sol, crystallite, liposome, cell, etc., which may or may not be further labeled with a dye, catalyst or other detectable group, and the like. The reporter molecule can be a fluorescent group such as fluorescein, a chemiluminescent group such as luminol, a terbium chelator such as N(hydroxyethyl) ethylenediaminetriacetic acid that is capable of detection by delayed fluorescence, and the like.

The label can generate a detectable signal either alone or together with other members of the signal producing system. As mentioned above, a reporter molecule can be bound directly to a nucleotide sequence or can become bound thereto by being bound to an specific binding pair (sbp) member complementary to an sbp member that is bound to a nucleotide sequence. Examples of particular labels or reporter molecules and their detection can be found in U.S. Pat. No. 5,508,178, the relevant disclosure of which is incorporated herein by reference. When a reporter molecule is not conjugated to a nucleotide sequence, the reporter molecule may be bound to an sbp member complementary to an sbp member that is bound to or part of a nucleotide sequence.

"Signal Producing System": A signal producing system as used herein means to a system that generates a signal that typically relates to the presence or amount of a target polynucleotide in a medium. A signal producing system may be incorporated on the oligonucleotide probes and relates to the presence of probes in a medium. Then signal producing system includes all of the reagents required to produce a measurable signal. Other components of the signal producing system may be included in the developer solution and can include substrates, enhancers, activators, chemiluminescent compounds, cofactors, inhibitors, scavengers, metal ions, specific binding substances required for binding of signal generating substances, and the like. Other components of the signal producing system may be coenzymes, substances that react with enzymic products, other enzymes and catalysts, and the like. The signal producing system provides a signal detectable by external means, by use of electromagnetic radiation, desirably by optical examination. Signal-producing systems that may be employed in the present invention are those described more fully in U.S. Pat. No. 5,508,178.

"Biological material": Biological material as used herein means to nucleic acids, such as DNA, RNA, polynucleotides, oligonucleotides, oligonucleotide probes, proteins, amino acids, antibodies, antigens, enzymes, coenzymes, ligands, receptors, hormones and labels, and monomers thereof, and genes that specify any of the above, and any other materials from any form of life and the synthetic versions of any of the above.

"Target", "Target sample", "Target material", or "biological target" as used herein means to the biological material, synthetic or natural, which is under test or to be assayed. The target may be a oligonucleotide, or portion thereof, complementary to the oligonucleotide probe; a complementary antigen, or portion thereof, to an antibody probe; a complementary antibody, or portion thereof, to an antigen probe; a complementary receptor or ligand, or portion thereof, to a respective ligand or receptor probe, for example.

"Sample" or "biological sample": Sample or biological sample as used herein means a portion of a biological material, either natural or synthetic, comprising one or more target materials. A sample may be blood, urine, tissue, etc., or a component thereof, for example, from a patient, either mammal, animal, bacterial, or viral, or any other form of life.

DETAILED DESCRIPTION OF PREFERRED EMBODIMENTS

The present invention provides a system and methods for assaying nucleic acid molecules in a biological sample. More specifically, the present invention provides a system and methods of detecting, sorting, tagging, tracking and characterizing nucleic acid molecules with reduced background signal and enhanced specificity and sensitivity. The present invention utilizes unstructured nucleic acids which have a reduced likelihood of hybridization with each other while maintaining their ability to hybridize with other nucleic acids. The use of unstructured nucleic acids in the present invention reduces the level of undesired cross hybridization in assays that rely upon correct hybridization between two nucleic acid molecules such as assays using nucleic acid arrays.

Currently, target-specific array-based hybridization assays utilize DNA arrays containing a set of oligonucleotides whose sequences are specifically designed to be complementary to potential nucleic acid targets in a biological sample (Chee, M., et al., (1996) Science 274, 610-614; Wang, et. al., Science, 280, 1077-1082). The set of oligonucleotides for the array are attached to a solid support (e.g. silicon, glass) such that different sequences of oligonucleotides can be differentiated by location. For example, each position on a glass slide corresponds to a specific nucleic acid sequence. In particular, a target-specific array for studying gene expression from two biological samples contains cDNA or oligonucleotides corresponding to genes of interest with the oligonucleotides having specifically designed sequences. The number of different genes being assayed can range from hundreds to thousands of sequences (see for example, Perou et al. Proc Natl Acad Sci USA 96(16):9212-7, 1999; Golub et al. Science 286(5439):531-7, 1999; Bittner et al. Nature 406(6795):536-40, 2000). Therefore, the number of different oligonucleotides to be synthesized for an array can be up to several thousands. The synthesized oligonucleotides are then attached to a solid support to produce the target-specific array.

The oligonucleotide probes may be synthesized, in situ, on the surface of an array (U.S. Pat. No. 5,847,105 & WO9525116) in either the 3' to 5' or 5' to 3' direction using the 3'-β-cyanoethyl-phosphoramidites or 5'-β-cyanoethyl-phosphoramidites and related chemistries known in the art (Beaucage et al., Tetrahedron Lett. 22:1859, 1981; Matteucci et al, J. Am. Chem. Soc. 103:3185, 1981; Caruthers et al. Method Enzymol. 154:287, 1987; and U.S. Pat. Nos. 4,415,732 and 4,458,066). In situ synthesis of the oligonucleotides may also be performed using photocleavable protecting groups (U.S. Pat. Nos. 5,424,186, 5,445,934, 6,022,963). In situ synthesis of the oligonucleotides may also be performed in the 5' to 3'direction using nucleotide coupling chemistries that utilize 3'-photoremovable protecting groups (U.S. Pat. No. 5,908,926).

Oligonucleotide probes may also be synthesized on the standard control pore glass (CPG) in the more conventional 3' to 5' direction using the standard 3'-β-cyanoethyl-phosphoramidites and related chemistries (Beaucage et al. Tetrahedron Lett. 22:1859, 1981; Matteucci et al. J. Am. Chem. Soc. 103:3185, 1981; Caruthers et al. Method Enzymol. 154:287, 1987; and U.S. Pat. Nos. 4,415,732 and 4,458,066) and incorporating a primary amine, thiol or aldehyde functional group onto either the 3' or 5' terminus of the oligonucleotide (Sproat et al. Nucleic Acids Res. 15:4837, 1987; Connolly and Rider. Nucleic Acids Res. 13:4485, 1985). The oligonucleotide may then be covalently attached to an appropriate array surface via the 3' or 5' termini using coupling chemistries known in the art (Strother et al. Nucleic Acids Res. 28(18):3535-3541, 2000; Zammatteo et al. Analytical Biochem. 280(1):143-150, 2000; Beier et al. Nucleic Acids Res. 27(9):1970-1977, 1999; ODonnell et al. Analytical Chem. 69(13):2438-2443, 1997).

Genotyping of single nucleotide polymorphisms (SNPs) using highly multiplexed DNA array-based methods are well known (for a review, see Syvanen. Human Mutation 13:1-10, 1999). For example, Pastinen et al. (Genome Research. 7:606-614, 1997) used oligonucleotide arrays to detect sequence mutations through single nucleotide primer extension of array-based oligonucleotides that hybridize adjacent to a sequence of interest in a target nucleic acid. Ross et al. (Nature Biotechnology. 16:1347-1351, 1998) describe multiplex genotyping using DNA arrays using mass spectrometry. In addition, a review by Hacia (Nature Genetics. 21:42-47, 1999) describes methods of resequencing and mutational analysis using DNA oligonucleotide arrays. These references describing SNP genotyping are incorporated herein by reference.

Assays using target-specific arrays detect the presence and levels of nucleic acid molecules having a sequence of interest by allowing the target nucleic acids to hybridize to the oligonucleotides in the array. In particular after hybridizing to probes on the array, the position and amounts of the target nucleic acids are determined using a signal molecule (e.g. radioactive, fluorescent, chemiluminescent). By determining the position of the signal on the array and correlating the position to the sequence of the oligonucleotides, information on the sequences of nucleic acid and the amounts in the sample is determined. In theory, direct measurements of the target nucleic acids in the sample are possible. However, in practice, disadvantages of the assay include cross hybridization between probes and unintended targets (non-cognate interactions) mediated through target-target interactions, and cross hybridization directly between probes and unintended targets. These types of non-cognate interactions introduce error into the measurements. Furthermore, the high cost of manufacturing target-specific arrays adds to the disadvantages of the method.

An alternative array-based method of analyzing nucleic acids has been described by several groups (Brenner U.S. Pat. No. 5,604,097; Morris et al. EP 97302313), and uses a universal spatially addressable array. In this method, the sequence of the oligonucleotides on an array are fixed, and thus are not tailored for each biological sample to be assayed. The universal nature of the arrays allows the same array design to be used with multiple samples having different target nucleic acid sequences.

To analyze and detect nucleic acids in a sample, methods using a fixed array design rely on the use of an intermediate nucleic acid molecule which hybridizes to a target nucleic acid molecule with one region ("anti-target") and also hybridizes to an oligonucleotide probe on the fixed array with another region ("tag"). The intermediary molecules therefore contain two domains that perform the two functions of 1) binding to a target molecule and 2) sorting the target molecules by binding to a spatially addressed probe ("anti-tag") on the fixed array. These two steps can be performed, in any order, separately or simultaneously. Thus the fixed array of oligonucleotides is designed to provide a substrate for sorting target molecules.

There are several advantages to the use of the fixed/universal array. One is that costly manufacturing of the array is only required for the fixed array. Therefore since the fixed array does not need to be designed specifically for the biological system being assayed, the fixed array can be mass-produced once the design of the oligonucleotides on the array is decided. In addition, the design and synthesis of the intermediary nucleic acid does not include the costly step of fixing the molecule onto a solid support. Therefore, intermediary molecules can be synthesized for each biological system of interest at a lower cost than the design and attachment of oligonucleotides of the target-based arrays.

The power and versatility of the universal fixed array is proportional to the number of spatially addressable anti-tag oligonucleotides on the array. However, as the number of oligonucleotides with different sequences increases, the likelihood of cross hybridization between multiple anti-tags, between multiple tags, and incorrect hybridization between an anti-tag and a tag also increases. A method of designing tag and anti-tag oligonucleotides that reduces multiple tag-to-anti-tag combinations is taught by Ben-Dor et al. (*J. of Comp. Biol.* 7(3-4):503-519, 2000) However, Ben-Dor et al. (supra) does not address the problem of cross hybridization between anti-target sequences of intermediary molecules and anti-tag sequences on the array.

Undesirable cross hybridization between anti-target sequences and anti-tag sequences reduces the signal and sensitivity of the assay by reducing the amount of intermediary molecules available for sorting target molecules, and also reduces the anti-tag sites available on the array for sorted target molecules. Therefore, cross hybridization between the array-bound anti-tag molecules and anti-target regions of intermediary molecules reduces the multiplexing rate obtainable by the universal tag system.

For example, in a six nucleotide region of an array bound oligonucleotide comprising A, T, G, and C, only 4096 sequences are possible for that six nucleotide region of the oligonucleotide. Therefore, in the universal tag system comprising anti-target sequences that are designed to assay a high number of target sequences, there is a likelihood that anti-target nucleic acids comprise sequences complementary to regions of the array-bound oligonucleotide. In particular, simulation studies conducted using uniformly drawn single nucleotide polymorphisms (SNPs; e.g amplicons of length 41 and a uniform middle base bi-allelic polymorphism) and multiplexing optimization heuristics show that only 25-30% of the sites on a universal fixed array are accessible when performing specific genotyping assays which interrogate 1000 samples.

The present invention therefore increases the multiplexing rate of assays utilizing universal fixed assays. Alternatively or additionally, use of UNAs in accordance with the present invention allows for the set of anti-tags to be decreased relative to the set used in conventional assays using universal fixed arrays which do not use UNAs. To date, there are no teachings that address the problem of cross-hybridization between anti-tag molecules and anti-target domains of the intermediary molecules.

An object of the present invention is to reduce the likelihood of cross-hybridization between anti-target sequences and anti-tag sequences without reducing the levels of hybridization between anti-tag probes and tag sequences, and between anti-target molecules and target biological molecules.

Therefore, it is an aspect of the present invention to provide a system and methods of analyzing nucleic acid molecules using universal spatially addressable arrays that have a reduced level of cross hybridization between anti-target regions of intermediary molecules and anti-tag probe molecules on the array. The present invention utilizes modified nucleotide base pairs called unstructured nucleotides or nucleic acids (UNA) to synthesize the anti-target regions of intermediary nucleic acid molecules and anti-tag nucleic acid molecules in an array such that the two molecules have a reduced likelihood of hybridizing to each other while still maintaining their ability to hybridize to their intended nucleic acid molecule (i.e. target/anti-target and tag/anti-tag molecules).

UNA nucleotides of the present invention are structurally modified to have a reduced ability to form a hydrogen-bonded base pair to its structurally modified Watson-Crick (W-C) complement. In addition, the modification(s) allows the modified nucleotide to form a base pair with its natural W-C complement or with an alternatively modified W-C complement. Therefore, polynucleotides containing UNA are capable of selectively hybridizing to a complementary polynucleotide without hybridizing to complementary polynucleotide having the same base sequence, but containing modifications of the base (UNAs)

In a base pair containing UNA nucleotides of the present invention, one or both of the nucleotides that form the base pair is substituted with a nucleotide containing a base analog so that the base pair is no longer formed, or is only formed at a reduced level. Preferably, the reduced level of base pairing is no more than one hydrogen bond interaction. In addition, the analog(s) is designed so that the nucleotide retains the ability to form a stable base pair with non-modified nucleotide complement or a non-UNA modified nucleotide complement.

The base pairing concepts of the present invention are schematically depicted by the following formulas where A'×T' and G'×C' represent disallowed base-pairing schemes, with the symbol x representing a reduced ability to form a base pair. [A*, T*, G*, and C*] represent a second group of bases capable of forming base pairs with A', T', G' and C' according to the general Watson-Crick base pair scheme of A-T and G-S, where - represents the ability to form a base pair. The same base pairing rules apply for RNA where U replaces T.

(1)

(2)

Formula 1 indicates that base pair analogs A'/T' and G'/C' have a reduced ability to form a stable base pair. However, as indicated in Formula 2, the bases of nucleotides A' T' G' and C' are capable of forming stable base pairs with a second group of nucleotide bases (A*T*G*C*). Therefore, nucleic acid molecules having modified nucleotides according the teachings of the present invention have a reduced ability to hybridize to other nucleic acid molecules also having modified nucleotides according to the present teachings.

Regions of nucleic acid molecules comprising UNAs may contain a mixture of nucleotide analogs and non-modified nucleotides. UNAs of the present invention may also contain only nucleotide base analogs. More specifically, in accordance with the base pairing formulas outlined in Formula 1 and 2, nucleotides of the first group (A', T', G', C') and nucleotides of the second group (A*, T*, G*, and C*) may include combinations of natural bases and modified bases or include all modified bases. For example, A' and T', which does not form a stable base pair, may be comprised of one nucleotide base analog (A') and one natural nucleotide (T'). Alternatively, A' and T' may be comprised of two nucleotide base analogs. Nucleotide pairs from the second group (e.g. A* and T*) may or may not form stable base pairs (A*-T* or A*×T*).

To provide non-limiting schematic examples of UNAs which contain mixtures of modified and natural bases, UNAs of the present invention may contain both A' and T' nucleotide analogs that do not form stable base pairs and also contain G and C nucleotides that do form stable base pairs. Alternatively, UNAs may contain G' and C' nucleotide analogs that do not form stable base pairs and also contain A and T nucleotides that do form stable base pairs. UNAs of the present invention may also contain both sets of analogs that do not form stable base pairs (A'×T' and G'×C'). For the present invention, nucleotides from the first and second class (e.g. A', A*) may be mixed in the same molecule. However, it is preferred that a single UNA molecule possess no more than one of each type of nucleotide (e.g. only A' T' G and C) which results in only one type of base-pairing scheme for each potential base-pair.

Selection of Nucleotides for UNAs

In accordance with the present invention, UNAs are produced such that substantially complementary sequence elements between two UNAs (or within one UNA) have a reduced ability to hybridize with each other. Nucleotides for producing UNAs are selected such that a first nucleotide base is not capable of forming a stable base pair with a nucleotide complement in a second nucleic acid molecule or in the same molecule. The two complementary nucleotides may have one naturally-occurring base and one base analog or may have two base analogs. The complementary nucleotides that are unable to form a stable base pair are used to produce UNAs with reduce the levels of hybridization by reducing intermolecular base pairing between sequence elements between UNAs that are substantially complementary. In particular as applied analytical methods using universal fixed nucleic acid arrays, UNAs reduce undesired hybridization between anti-target regions of intermediary molecules and anti-tag probes of the arrays.

UNAs of the present invention maintain the ability to hybridize to their intended complementary molecules. For example, anti-tag probes having UNAs maintain the ability to hybridize to tag regions of intermediary molecule yet have a reduced ability to hybridize to anti-target regions of the intermediary molecule. Anti-target regions of intermediary molecules maintain the ability to hybridize to target nucleic acid molecules in a biological sample yet have a reduced ability to hybridize to anti-tag probes in the universal spatially addressable arrays.

2-Aminoadenosine (D), 2-Thiothymidine (2-thioT), Inosine (I) and Pyrrolo-pyrimidine (P)

In a preferred embodiment of the present invention, the nucleotide analogs 2-aminoadenosine (D), 2-thiothymidine (2-thioT), inosine (I) and pyrrolo-pyrimidine (P) are used to generate a nucleic acid molecule (such as an anti-tag or anti-target region of a molecule) that has a reduced ability to cross hybridize with another nucleic acid molecule having sequence elements substantially complementary to sequence elements in the first nucleic acid molecule. In addition UNAs of the present invention, while unable to cross hybridize with each other, maintain the ability to hybridize with their intended nucleic acid complements. The structures of the D/2-thioT, I/P and the four natural base pairs along with various combinations of the natural and base analogs are shown in FIG. 3.

Figure 1B:
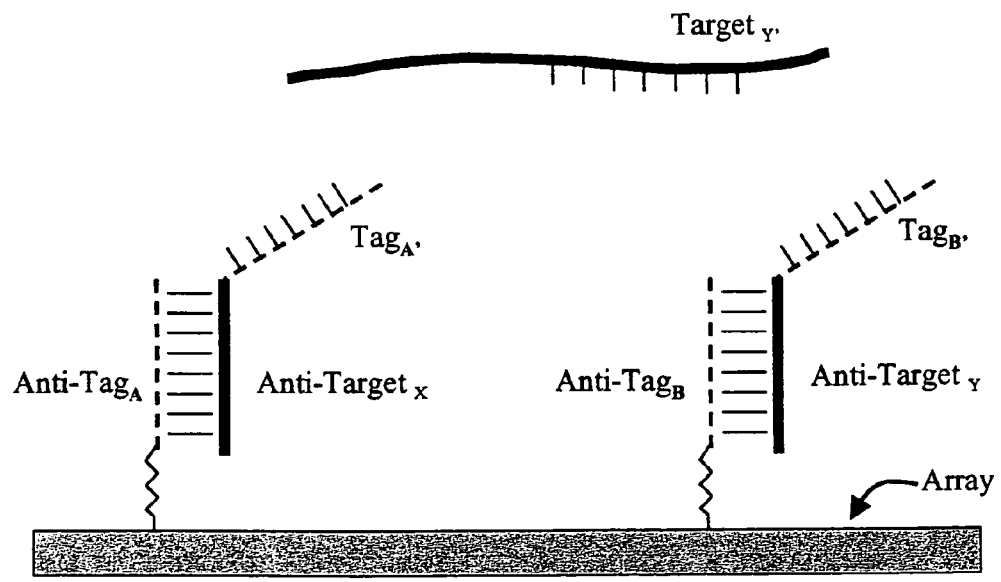
Figure 2:
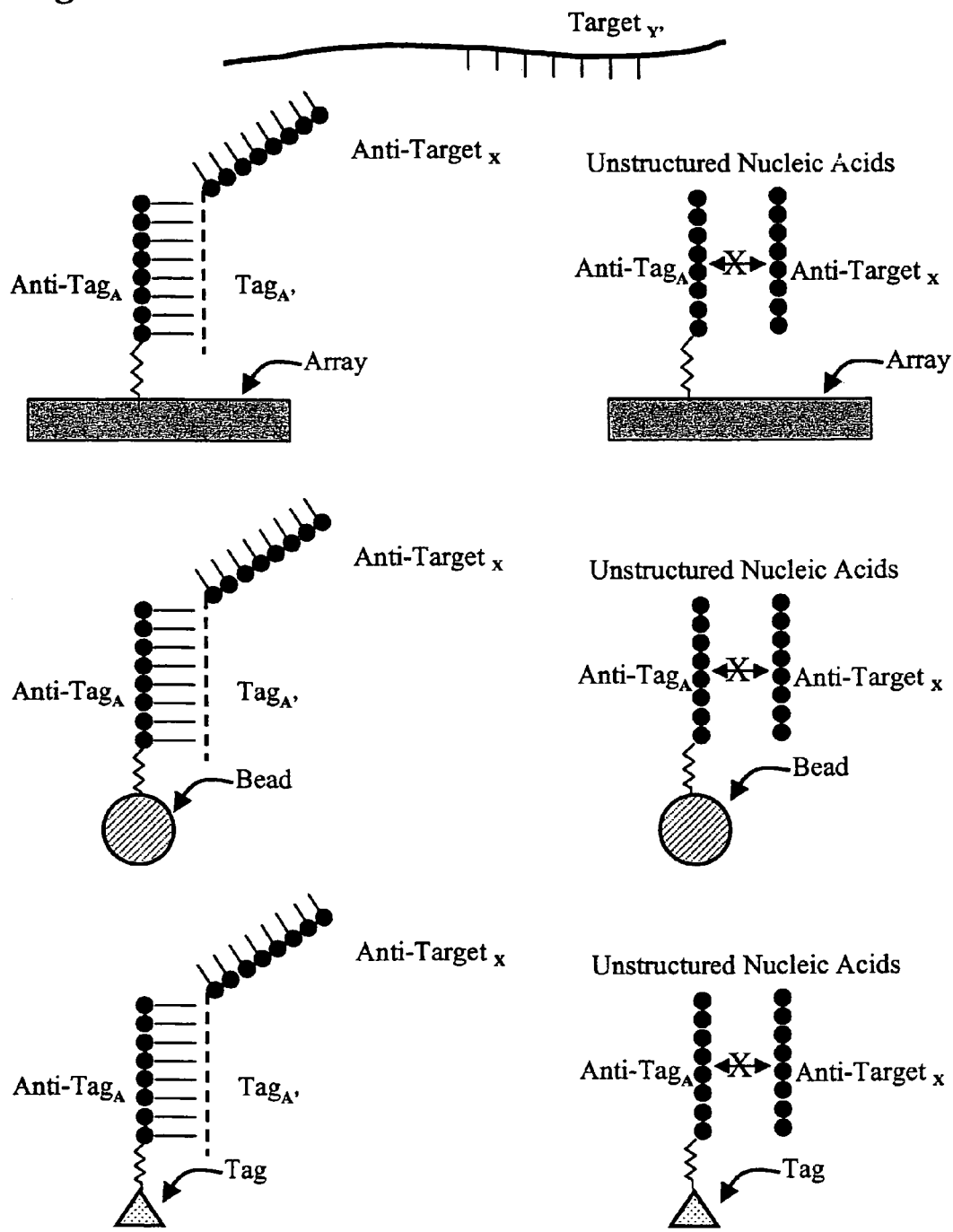
FIG. 2 is a schematic representation of the use of Unstructured Nucleic Acids (UNA) (dark filled circles) to eliminate possible mishybridization between the $Anti-Tag_A$ oligonucleotide on the array and the $Anti-Target_X$ region of the intermediate molecule.

Naturally occurring Watson-Crick base-pairing is defined by specific hydrogen bonding interactions between the bases of adenine and thymine (or uracil) and between guanine and cytosine. Positioning of hydrogen-bond donors (e.g. amino groups) and hydrogen-bond acceptors (e.g. carbonyl groups) on purine and pyrimidine bases place structural constraints on the ability of two nucleoside bases to form stable hydrogen bonds. FIG. 1 shows the structures of the bases and the relative orientations of the bases to each other in a Watson-Crick base pair. In addition, an inosine:cytosine base pair is shown. The inosine-cytosine base pair is identical to a G-C base pair except that the I-C base pair lacks the hydrogen bond donor of the 2-amino group of guanine which is missing in inosine.

Therefore, regions of a UNA containing 2-aminoadenosine have a reduced likelihood of hybridizing to complementary regions of another UNA (or the same UNA) containing 2-thiothymidine. However, the regions of UNAs having 2-aminoadenosine maintain a level of hybridization to complementary regions of nucleic acids containing natural thymidine nucleotides. Furthermore, regions of a UNA containing inosine have a reduced likelihood of hybridizing to complementary regions of another UNA (or the same UNA) containing pyrrolo-pyrimidine. However, the regions of UNAs having inosine maintain an ability to hybridize to complementary regions of nucleic acids containing natural guanosine nucleotides.

2-Aminoadenosine (D), 2-Thiothymidine (2-thioT)

Without being limited by theory, a D/2-thioT base pair analog is prevented from forming a stable base pair presumably due to a steric clash between the 2-thio group of 2-thioT and the exocyclic amino group of 2-aminoadenosine as a result of the larger atomic radius of the sulfur atom. This tilts the nucleotide bases relative to one another such that only one hydrogen bond is able to form. It is also known that thionyl sulfur atoms are poorer hydrogen-bonding acceptors than carbonyl oxygen atoms which could also contribute to the weakening of the D/2-thioT base pair.

The 2-aminoadenosine (D) nucleotide is capable of forming a stable base-pair with thymidine (T) through three hydrogen bonds in which a third hydrogen bonding interaction is formed between the 2-amino group and the C2 carbonyl group of thymine. As a result, the D/T base pair is more stable thermodynamically than an A/T base pair. In addition, 2-thiothymidine (2-thioT) is capable of forming a stable hydrogen bonded base pair with adenosine (A) which lacks an exocyclic C2 group to clash with the 2-thio group.

Therefore, UNA oligonucleotide and polynucleotide molecules with 2-aminoadenosine (D) and 2-thioT replacing A and T respectively have a reduced ability to form intermolecular and intramolecular base pairs with UNAs having also having D and 2-thioT nucleotides but are still capable of hybridizing to oligonucleotides and polynucleotides of substantially complementary sequence comprising A and T and lacking D and 2-thioT. Without being limited by theory, the aforementioned proposed mechanisms regarding the factors responsible for stabilizing and disrupting the A/T and G/C analogue pairs are not meant in anyway to limit the scope of the present invention and are valid irrespective of the nature of the specific mechanisms.

Gamper and coworkers (Kutyavin et al. *Biochemistry*, 35; 11170 (1996) determined experimentally that short oligonucleotide duplexes containing D/T base pairs that replace A/T base pairs have melting temperatures (Tm) as much as 10° C. higher than duplexes of identical sequence composed of the four natural nucleotides. This is due mainly to the extra hydrogen bond provide by the 2-amino group. However, the duplexes designed to form opposing D/2-thioT base-pairs exhibited Tms as much as 25° C. lower than the duplex of identical sequence composed of standard A/T base-pairs. The authors speculate that this is mainly due to the steric clash between the 2-thio group and the 2-amino group which destabilizes the duplex. Deoxyribonucleotides in this study were synthesized using chemical methods.

Although the base-pairing selectivity for these analog pairs has been experimentally tested for only DNA duplexes, it is likely that these same rules will hold for RNA duplexes and DNA/RNA heteroduplexes as well. This would allow for RNA versions of UNAs to be generated by transcription of PCR or cDNA products using the ribonucleotide triphosphate forms of the UNA analog pairs and RNA polymerases.

Inosine (I) and Pyrrolo-pyrimidine (P)

The inosine (I) and pyrrolo-pyrimidine (P) I/P base pair analog is also depicted in FIG. 3. Inosine, which lacks the exocyclic 2-amino group of guanine, forms a stable base pair with cytosine through two hydrogen bonds (vs. three for G/C). The other member of the I/P analog is pyrrolo-pyrimidine (P) which is capable of forming a stable base pair with guanine despite the loss of the 4-amino hydrogen bond donor of cytosine. FIG. 1 shows that a P/G base pair is also formed through two hydrogen bonds. The N7 group of P is spatially confined by the pyrrole ring and is unable to form a hydrogen bond with the C6 carbonyl O of guanine. However, this does not prevent the formation of the other two hydrogen bonds between P/G. The I/P base pair is only capable of forming one hydrogen bond (as depicted in FIG. 1) and is therefore not a stable base pair. As a result, UNA polynucleotide molecules with I and P replacing G and C respectively are unable to form intermolecular and intramolecular I/P base pairs and therefore have a reduced ability to hybridize to UNA molecules containing I and P. Moreover, UNAs having I and P maintain the ability to hybridize to oligonucleotide and polynucleotide molecules of substantially complementary sequence comprising G and C and lacking I and P.

Woo and co-workers (Woo et al., *Nucleic Acids Research*, 24; 2470 (1996) showed that introducing either P or I into 28-mer duplexes to form P/G and I/C base-pairs decreased the Tm of the duplex by −0.5 and −1.9° C respectively per modified base-pair. These values reflect the slight destabilization attributable to the G/P pair and a larger destabilization due to the I/C pair. However, introducing P and I into the duplexes such that opposing I/P base-pairs are formed reduced the Tm by −3.3° C. per modified base-pair. Therefore the I/P base pairs are more destabilizing.

Synthesis of UNAs

Those skilled in the art of nucleic acids synthesis readily appreciate methods of synthesizing anti-tag UNA and anti-target regions of intermediary molecules using chemical or enzymatic methods according to the teachings herein. In particular for chemical methods, Gampers et al. (supra) and Woo et al. (supra) both teach the chemical synthesis of complementary oligonucleotides containing modified nucleotides and demonstrates that the oligonucleotides have a reduced ability to hybridize to each other compared to oligonucleotides with non-modified nucleotides having the same base sequence.

In general, oligonucleotide and polynucleotide UNAs in accordance with the present invention which contain modified nucleotides may be synthesized by chemical or enzymatic methods. Various techniques can be employed for preparing an oligonucleotide. Such oligonucleotides can be obtained by biological synthesis or by chemical synthesis. For short sequences (up to about 100 nucleotides), chemical synthesis will frequently be more economical as compared to the biological synthesis. In addition to economy, chemical synthesis provides a convenient way of incorporating low molecular weight compounds and/or modified bases during specific synthesis steps. Furthermore, chemical synthesis is very flexible in the choice of length and region of target polynucleotides binding sequence. The oligonucleotide can be synthesized by standard methods such as those used in commercial automated nucleic acid synthesizers. Chemical synthesis of DNA on a suitably modified glass or resin can result in DNA covalently attached to the surface. This may offer advantages in washing and sample handling. For longer sequences standard replication methods employed in molecular biology can be used such as the use of M13 for single stranded DNA as described in J. Messing (1983) *Methods Enzymol.* 101:20-78.

In situ synthesis of oligonucleotide or polynucleotide probes on the substrate is performed in accordance with well-known chemical processes, including, but not limited to sequential addition of nucleotide phosphoramidites to surface-linked hydroxyl groups, as described by T. Brown and Dorcas J. S. Brown in *Oligonucleotides and Analogues A Practical Approach*, F. Eckstein, editor, Oxford University Press, Oxford, pp. 1-24 (1991). Indirect synthesis may be performed in accordance biosynthetic techniques (e.g. polymerase chain reaction "PCR"), as described in Sambrook, J. et al., "Molecular Cloning, A Laboratory Manual", 2$^{nd}$ edition 1989, incorporated herein by this reference.

Also, the oligonucleotide probes may be synthesized, in situ, on the surface of an array (U.S. Pat. No. 5,847,105 & WO9525116) in either the 3' to 5' or 5' to 3' direction using the 3'-β-cyanoethyl-phosphoramidites or 5'-β-cyanoethyl-phosphoramidites and related chemistries known in the art (Beaucage et al. *Tetrahedron Lett.* 22;1859 (1981); Matteucci et al. *J. Am. Chem. Soc.* 103;3185 (1981); Caruthers et al. *Method Enzymol.* 154; 287 (1987); U.S. Pat. Nos. 4,415,732 and 4,458,066). In situ synthesis of the oligonucleotides may also be performed using photocleavable protecting groups (U.S. Pat. Nos. 5,424,186, 5,445,934, 6,022,963). In situ synthesis of the oligonucleotides may also be performed in the 5' to 3' direction using nucleotide coupling chemistries that utilize 3'-photoremovable protecting groups (U.S. Pat. No. 5,908,926).

Other methods of oligonucleotide synthesis include, but are not limited to solid-phase oligonucleotide synthesis according to the phosphotriester and phosphodiester methods (Narang, et al., (1979) *Meth. Enzymol.* 68:90), and to the H-phosphonate method (Garegg, P. J., et al., (1985) "Formation of inter-nucleotidic bonds via phosphonate intermediates", *Chem. Scripta* 25, 280-282; and Froehler, B. C., et al., (1986a) "Synthesis of DNA via deoxynucleoside H-phosphonate intermediates", *Nucleic Acid Res.*, 14, 5399-

5407, among others) and synthesis on a support (Beaucage, et al. (1981) *Tetrahedron Letters* 22:1859-1862) as well as phosphoramidate techniques (Caruthers, M. H., et al., "Methods in Enzymology," Vol. 154, pp. 287-314 (1988) and others described in "Synthesis and Applications of DNA and RNA," S. A. Narang, editor, Academic Press, New York, 1987, and the references contained therein, and nonphosphoramidite techniques. The chemical synthesis via a photolithographic method of spatially addressable arrays of oligonucleotides bound to glass surfaces is described by A. C. Pease, et al., *Proc. Natl. Aca. Sci. USA* (1994) 91:5022-5026. Oligoribonucleotide synthesis using phage RNA polymerase and ribonucleoside triphosphates is described by Milligan, J. F., et al., (1987) "Oligoribonucleotide synthesis using T7 RNA polymerase and synthetic DNA templates", *Nucl. Acids Res.* 15, 8783-8798; and using protected ribonucleoside phosphoramidites and chemical synthesis is described by Wu T., et al., (1989) "Prevention of chain cleavage in the chemical synthesis of 2'-O-silylated oligoribonucleotides", *Nucl. Acids Res.* 17, 3501-3517, among others.

Oligonucleotide probes may also be synthesized on the standard control pore glass (CPG) in the more conventional 3' to 5' direction using the standard 3'-β-cyanoethyl-phosphoramidites and related chemistries (Beaucage et al. *Tetrahedron Lett.* 22;1859 (1981); Matteucci et al. *J. Am. Chem. Soc.* 103;3185 (1981); Caruthers et al. *Method Enzymol.*, 154; 287 (1987); U.S. Pat. Nos. 4,415,732 and 4,458, 066) and incorporating a primary amine, thiol or aldehyde functional group onto either the 3' or 5' terminus of the oligonucleotide (Sproat et al. *Nucleic Acids Res.* 15; 4837 (1987); Connolly and Rider, *Nucleic Acids Res.* 13;4485 (1985)). The oligonucleotide may then be covalently attached to an appropriate array surface via the 3' or 5' termini using coupling chemistries known in the art (Strother et al. *Nucleic Acids Res.*, 28(18):3535-3541 (2000); Zammatteo et al. *Analytical Biochem.* 280(1):143-150 (2000); Beier and Hoheisel, *Nucleic Acids Res.* 27(9): 1970-1977 (1999); ODonnell et al. *Analytical Chem.* 69(13): 2438-2443 (1997)). The density of the oligonucleotides on the array surface can range from about 1,000 to 200,000 probe molecules per square micron. The probe density can be controlled by adjusting the density of the reactive groups on the surface of the electrode for either the in situ synthesis post-synthesis deposition methods.

Without limiting the scope of the present invention to only the modified nucleotides discussed herein, the synthesis of polynucleotides containing the modified nucleotides discussed in the Examples is described to provide experimental detail. In particular, Sampson (U.S. Ser. No. 09/358,141) teaches the enzymatic synthesis of UNAs using modified nucleotides and DNA polymerases and is incorporated herein by reference. Sampson demonstrates that modified nucleotide precursors are incorporated into polynucleotides by polymerases to form polynucleotides that are on the order of 100 to several kilobases in length.

Enzymatic Synthesis of UNAs Comprising D, 2-thioT, I, and P

In an embodiment of the present invention, nucleic acid molecules with reduced levels of undesired cross hybridization are generated by performing primer dependent, template directed polymerase reactions using the nucleotide 5'triphosphate forms of the appropriate analog pairs. These include; 2-amino-2'deoxyadenosine-5'-triphosphate (dDTP), 2-thiothymidine-5'-triphosphate (2-thioTTP), 2'-deoxyinosine-5'-triphosphate (dITP) and 2'-deoxypyrrolo-pyrimidine-5'triphosphate (dPTP). For example, a reaction containing dDTP, 2-thioTTP, dCTP and dGTP will generate UNAs which are unable to form intermolecular and intramolecular D/2-thioT base pairs. Likewise, a reaction containing dATP, dTTP, dPTP and dITP will generate UNAs which are unable to form intermolecular and intramolecular P/I (modification of G/C) base pairs. A polymerization reaction containing both analog pairs, dDTP, 2-thioTTP; and dPTP, dITP will generate UNAs that have no predicted intramolecular and intermolecular base-pairing interactions with other UNAs containing the same modified bases. However, since 2-aminoadenosine, 2-thiothymidine, pyrrolo-pyrimidine, and inosine are still capable of forming stable base pairs with thymidine, adenosine, cytidine and guanosine respectively, all three types of UNAs should be able to specifically hybridize intermolecularly to oligonucleotides composed of the four natural bases.

It is recognized that UNAs of the present invention may have a reduced ability to hybridize to other UNAs. For example, UNAs having D, 2-thioT, G and C may be capable of hybridizing regions of substantial complementary in the same molecule or in another UNA in regions that are rich in G and C sequences. Furthermore, UNAs having A, T, pyrrolo-pyrimidine, and inosine may be capable of hybridizing to regions of substantial complementary in the same molecule or in another UNA in regions that are rich in A and T sequences. It is recognized that the levels of hybridization may be controlled by one skilled in the art by using different amounts of natural nucleotides and modified nucleotides according to the teachings herein.

As described above, but without limitations to only those experimental conditions, UNAs potentially containing only G/C intramolecular and intermolecular base pairs are generated by enzymatically incorporating the triphosphate forms of 2-aminoadenosine, 2-thiothymidine, guanosine, and cytosine into a polynucleotide. The resulting UNA polynucleotide is not capable of forming intramolecular and intermolecular A/T base pairs, but is still capable of forming intramolecular and intermolecular G/C base pairs.

The aforementioned mechanisms which may account for the observed disruption of the A/T and G/C analogue pairs is not meant in anyway to limit the scope of the present invention and is valid irrespective of the nature of the specific mechanisms.

Enzymatic Synthesis of UNAs Comprising D, 2-thioT, 2-thioC, and G

In yet another preferred embodiment, the nucleic acid molecules of the present invention are enzymatically generated by primer dependent polymerase reactions using the 5'-triphosphate forms of D/2-thiothymidine and 2-thiocytosine/guano sine (2-thioC/G). UNAs comprising D/2-thioT and 2-thioC/G have a reduced ability to hybridize to other nucleic acid molecules (UNAs) also containing D/2-thioT and 2-thioC/G and yet maintain their ability to hybridize with oligonucleotide and polynucleotide molecules comprising adenosine, thymidine, cytosine and inosine as a substitute for G. 2-thioC and G are unable to form a stable base pair. The presence of a 2-thiol exocyclic group in cytosine replacing the C2 carbonyl group effectively removes the hydrogen bond acceptor at that position and causes a steric clash due to the large ionic radius of sulfur as compared to oxygen. As a result, 2-thioC/G is only capable of forming a single hydrogen bond and is thus not a stable base pair. However, 2-thioC and I are capable of forming a stable base pair through two hydrogen bonds since the removal of the 2-amino exocyclic group of guanine that results in inosine effectively removes the steric clash between the C2 sulfur of 2-thioC and the 2-amino group of guanine.

Therefore, UNA polynucleotide molecules with reduced levels of intermolecular cross hybridization and intramolecular hybridization are generated enzymatically using the 5'-triphosphate forms of the base pair analogs. These include; 2-amino-2'-deoxyadenosine-5'-triphosphate (dDTP), 2-thiothymidine-5'-triphosphate (2-thioTTP), 2'-deoxyguanosine-5'-triphosphate (dGTP) and 2-thio-2'-deoxycytidine-5'-triphosphate (2-thio-dCTP). For example, a reaction with 2-thio-dCTP, dGTP, dATP, dTTP will generate UNAs that can form only A/T base pairs. A polymerization reaction containing both analog pairs, 2-thio-dCTP/dGTP, and dDTP/2-thioTTP will generate UNAs that have no predicted intramolecular and intermolecular base-pairing interactions with each other. However, since 2-aminoadenosine, 2-thiothymidine, 2-thiocytidine and guanosine are still capable of forming stable base pairs with thymidine, adenosine, inosine and cytidine respectively, UNAs comprising (A, T, 2-thioC, G) or (D, 2-thioT, 2-thioC, G) should be able to specifically hybridize to oligonucleotides (probes) composed of the appropriate bases according to the base pairing rules discussed.

The 2-thioC/G base pair analog provides an example of a base pair analog comprising a natural nucleotide base and a nucleotide base analog which can not form a stable base pair. As previously stated, polynucleotides containing 2-thiocytidine and guanosine cannot form intramolecular or intermolecular 2-thioC/G base pairs. However, these polynucleotides can form base pairs with polynucleotides of substantially complementary sequences through 2-thioC/I and C/G base pairs. Therefore, UNAs comprising 2-thioC/G are capable of hybridizing to polynucleotide molecules also containing base analogs (inosine).

Those of skill in the art will readily appreciate other modifications to nucleic acid bases, sugars and the phosphate backbone that will not affect the teachings of the present invention. Furthermore, modifications of the bases that affect the general base pair schemes as described in Formulas 1 and 2 are within the scope of the present invention. The following Examples illustrate methods of synthesizing UNAs enzymatically are not meant to limit the scope of the present invention to only the teachings of the Examples. As previously discussed, UNAs for use in the present invention may also be synthesized chemically by methods known in the art.

EXAMPLE 1

Figure 4:
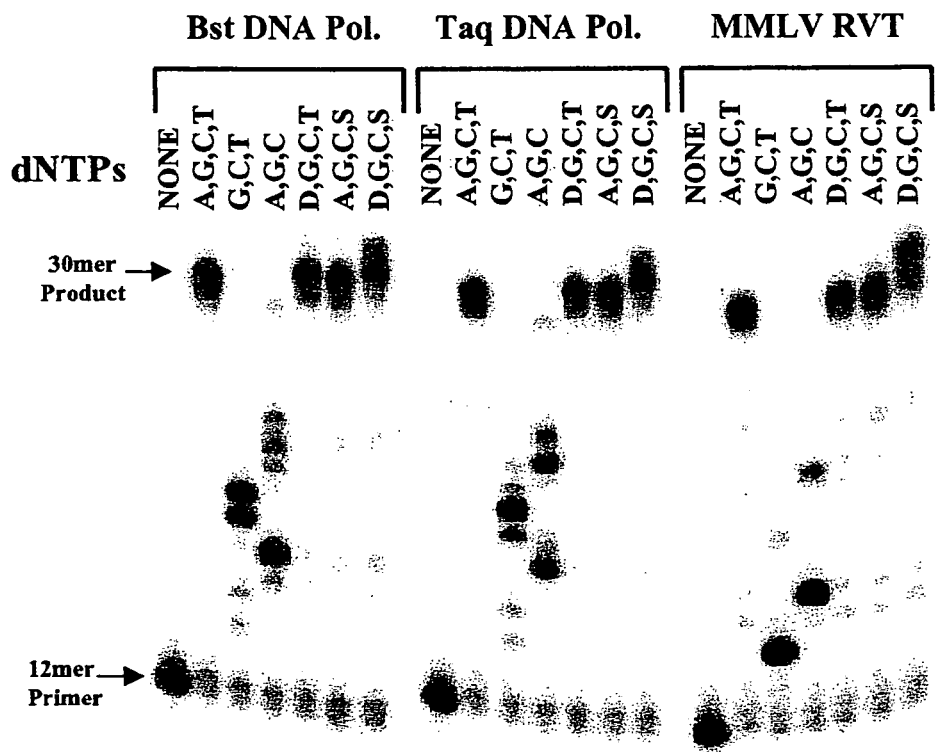
FIG. 4 shows a DNA primer/template sequence used for the polymerase extension reaction.

Incorporation of the 2-amino-2'-deoxyadenosine-5'-triphosphate and 2-thiothymidine-5-triphosphate into Polynucleotides by DNA Polymerases The ability of the *Bacillus sterothermophilus* (Bst) DNA polymerase (New England Biolabs), the *Thermus aquaticus* (Taq) DNA polymerase (Amersham) and the Moloney Murine Leukemia Virus reverse transcriptase (MMLV-RT) (Amersham) to incorporate the dDTP and 2-thioTTP into polynucleotides was tested using a synthetic 30-mer template and $^{32}$P-labeled 12-mer primer (S.A. 130 Cl/mmol). (FIG. 4). Extension reactions for each polymerase were performed in 0.65 ml pre-siliconized microfuge tubes containing the following components: (Bst) 20 mM Tris-Cl (pH 8.8 @25° C.), 10 mM KCl, 10 mM $(NH_4)_2SO_4$, 2 mM $MgSO_4$, 0.1% Triton-X100, 0.5 microM primer/template, 250 microM each dNTP and 0.15 units/microL Bst DNA polymerase; (Taq) 26 mM Tris-Cl (pH 9.5 @25° C.), 6.5 mM $MgCl_2$, 0.5 microM primer/template, 250 microM each dNTP and 0.15 units/microL Taq DNA polymerase; (MMLV-RT) 50 mM Tris-Cl (pH 8.3 @25° C.) 75 mM KCl, 3 mM $MgCl_2$, 1 M DTT, 0.5 microM primer/template, 250 microM each dNTP and 0.5 units/microL MMLV-RT. The reactions were incubated for 15 minutes at 65° C. for the Bst and Taq reactions and 42° C. for the MMLV-RT reaction. The reaction mixtures were separated by electrophoresis on 10% denaturing (7M urea) polyacrylamide gels and visualized by phosphorimaging methods.

In the reaction mixtures containing only dGTP, dCTP, dTTP or dATP, dGTP and dCTP, no full-length product was generated by any of the three polymerases (FIG. 4B). However, when all four dNTPs were present or when dDTP (D) was substituted for dATP or 2-thioTTP (S) was substituted for dTTP, greater than 90% of the primer was converted to full-length 30-mer product. The incorporation of the dDTP by the Taq DNA polymerase is consistent with the results of Bailly and Waring (*Nucleic Acids Research*, 23:885. 1995). Importantly, full-length product was generated by all three polymerases when both the D and S are substituted for A and T in a single reaction mixture.

To further assess the incorporation efficiency of the modified nucleotides by Bst DNA polymerase, the efficiency for a single nucleotide extension reaction was determined using two 6-mer primers in the presence of varying concentrations of dATP, dDTP, dTTP or 2-thioTTP (FIGS. 5A and 6A). For this study, the reaction mixtures contained; 20 mM Tris-Cl (pH 8.8 @25° C.), 10 mM KCl, 10 mM $(NH_4)_2SO_4$, 2 mM $MgSO_4$, 0.1% Triton-X100, 500 nanoM 6-mer primer, 20 nanoM 30-mer DNA template, 0.8 units/microL (~70 nanoM) Bst DNA polymerase and a dNTP concentration ranging from 0.5 microM to 130 microM. The reaction mixtures were incubated at 45° C. for 8 hours and separated by electrophoresis on 20% denaturing (7M urea) polyacrylamide gels.

The GACTGA 6-mer primer is extended with dATP and dDTP (D) with approximately equal efficiencies (FIGS. 5B & C). Likewise, the extension efficiency of the GCTCTG 6-mer primer with the dTTP and 2-thioTTP (S) are also very similar and exhibit a 50% incorporation at about 4 and 6 microM respectively (FIGS. 6B & 6C). These results indicate that the dDTP and 2-thioTTP are both very good substrates for the Bst DNA polymerase and possess $k_{cat}/K_m$ values near that of their natural counterparts.

To establish that the extension products generated in the presence of the dDTP and 2-thioTTP were not due to contaminating dATP and dTTP in the dDTP and 2-thioTTP preparations, a mass spectroscopic analysis was performed on the extension reaction mixtures using the 6-mer primers (FIG. 7A). The extension reactions were performed in 0.65 ml pre-siliconized microfuge tubes containing the following components; 20 mM Tris-Cl (pH 8.8 @25° C.), 10 mM KCl, 10 mM $(NH_4)_2SO_4$, 2 MM $MgSO_4$, 0.1% Triton®-X 100, polyethylene glycol tert-octylphenyl ether (also referred to as t-octylphenoxypolyethoxyethanol), 500 nM 6-mer primer, 20 nM 30-mer DNA template, 0.8 units/microL (~70 nM) Bst DNA polymerase and 20 microM dNTP. The reaction mixtures were incubated at 45° C. for 4 hours and quenched with EDTA. 5 microL of the reaction mixture was mixed with 15 microL of distilled $H_2O$ and 20 microL of matrix solution (0.2 M 2,6-dihydroxyacetophenone, 0.2 M diammonium hydrogen citrate). One microliter samples were spotted and dried on a MALDI sample grid plate analyzed by Matrix Assisted Laser Desorption Ionization Time-of-Flight (MALDI-TOF) mass spectrometry.

The reaction mixtures containing the 6-mer primer GACTGA and either dATP or dDTP give single extension products having m/z values of 2130.2 and 2146.0 respectively (FIG. 7B). This results in a 15.8 amu difference between the two 7-mer extension products which is consistent with the mass difference between the adenosine and the 2-aminoadenosine bases (FIG. 7C). Likewise, the reaction mixtures containing the 6-mer primer GCTCTG and either dTTP or 2-thioTTP (S) give single extension reaction products having m/z values of 2089.7 and 2106.1 respectively. The resulting 16.4 amu difference between these two 7-mer extension products is consistent with the mass difference between the thymidine and 2-thiothymidine bases (FIG. 7C). These results conclusively show that both the 2-aminoadenosine and 2-thiothymidine nucleotides triphosphates are indeed incorporated by the Bst DNA polymerase and that the dDTP and 2-thioTTP preparations do not contain any contaminating dATP and dTTP respectively.

EXAMPLE 2

Synthesis of Single Stranded Polynucleotides

Unstructured single stranded UNA was generated by incorporating 2-aminoadenosine and 2-thiothymidine nucleotides using a 14-mer primer and 56-mer template (5'-phosphorylated) and Bst DNA Polymerase followed by digestion of the DNA template with Lambda Exonuclease (FIG. 8). Ten microliter extension reactions were performed in 0.65 ml pre-siliconized microfuge tubes containing the following components; 20 mM Tris-Cl (pH 8.8 @25° C.). 10 mM KCl, 10 mM $(NH4)_2SO_4$, 2 mM $MgSO_4$, 0.1% Triton®-X100 polyethylene glycol tert-octylphenyl ether (also referred to as t-octylphenoxypolyethoxyethanol), 1.0 microM primer/template, 500 microM dGTP, 500 microM dATP (or dDTP), 500 microM dTTP (or 2-thioTTP), 200 microM $^{32}$P-CTP and 0.8 units/microL Bst DNA polymerase. The reactions were incubated at 65° C. for 30 minutes, quenched with 5 mM EDTA, ethanol precipitated, dried and resuspended in 10 microL of 10 mM Tris-Cl pH 8.0. The 56-mer template was digested by incubating the resuspended samples with 10 units of lambda exonuclease (Strandase Kit™, (Novagen; Madison, Wis.)) for 30 minutes at 37° C. The reactions were quenched with 5 mM EDTA, ethanol precipitated, dried and resuspended in 10 microL of 10 mM Tris-Cl pH 8.0. The samples were then electrophoresed on 10% denaturing (7M urea) polyacrylamide gels and visualized using phosphorimaging methods.

Figure 9:
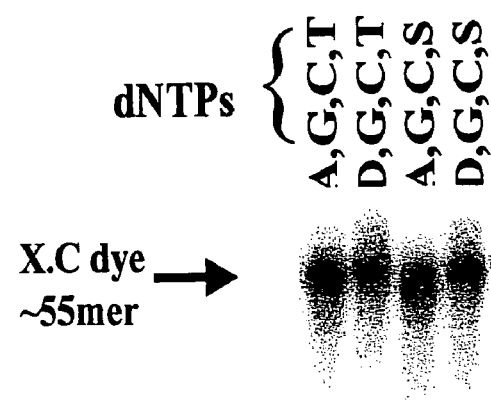
FIG. 9 shows a 10% denaturing PAGE analysis of the single-stranded polynucleotides containing the indicated nucleotides. The size marker dyes are indicated with arrows.

As shown in FIG. 9, full-length 56-mer product is generated in the presence of either the four standard dNTPs or when dDTP (D) and 2-thioTTP (S) are substituted for dATP and dTTP respectively. In addition, little if any premature termination products are generated in the reactions containing dDTP and 2-thioTTP. Thus because the DNA template sequence includes three tandem A and T residues (Bold text in FIG. 8), the results show that the Bst DNA polymerase can efficiently incorporate the 2-aminoadenosine and 2-thiothymidine nucleotides at adjacent sites in the polynucleotide product.

We claim:

1. A method of assaying target nucleic acid molecules comprising the steps of
   a) providing a first plurality of nucleic acids, wherein at least one region of the nucleic acids in the first plurality is designed to be complementary to a nucleotide sequence of a second plurality of nucleic acids, wherein the first plurality of nucleic acids is immobilized on a surface such that different sequences of the first plurality of nucleic acids are spatially addressed and can be differentiated by location and wherein the nucleic acid at each location has a different nucleotide sequence than nucleic acids at other locations;
   b) providing said second plurality of nucleic acids, wherein the nucleotide sequence of each nucleic acid of the second plurality is known and comprises a first region and a second region, wherein each first region of each nucleic acid of the second plurality has a different nucleotide sequence from other first regions of other nucleic acids of the second plurality, wherein each first region of nucleic acids of the second plurality is designed to be complementary to a nucleotide sequence of nucleic acids of the first plurality, wherein at least one second region of the nucleic acids in the second plurality is complementary to a target nucleic acid in a biological target, wherein each nucleic acid of the first plurality and each second region of each nucleic acid of the second plurality comprises unstructured nucleotides such that the second region has a reduced ability to hybridize to a first nucleic acid of the first plurality having a complementary nucleotide sequence without reducing the ability of the second region of each nucleic acid of the second plurality to hybridize to a complementary nucleic acid molecule in a biological target;

c) providing a biological target containing nucleic acids to be analyzed;

d) contacting the biological target with the second plurality of nucleic acids under conditions that permit hybridization of complementary nucleotide sequences between the target nucleic acid molecules and the second region of nucleic acids of the second plurality;

e) contacting the second plurality of nucleic acids with the first plurality of nucleic acids under hybridization conditions;

f) detecting nucleic acids in the biological target that have hybridized to a nucleic acid of the second plurality by detecting a signal of a label that is part of the nucleic acids of the biological target;

g) determining a location of the detectable signal of the label on the surface; and h) determining the nucleotide sequence of the nucleic acid in the biological target that has hybridized to a nucleic acid of the second plurality by correlating the location of the signal to the nucleotide sequence.

2. The method of claim 1, wherein the steps of (d) and (e) are performed simultaneously.

3. The method of claim 1, wherein after step (e), unhybridized nucleic acids are removed.

4. The method of claim 1, wherein the step of detecting the label further comprises detecting the label by measuring light emission from the label.

5. The method of claim 1, wherein the step of contacting the biological sample with the second plurality of nucleic acids further comprises labeling the nucleic acids that having hybridized with a nucleic acid in the sample with a detectable label.

* * * * *

SEQUENCE LISTING

<160> NUMBER OF SEQ ID NOS: 8

<210> SEQ ID NO 1
<211> LENGTH: 6
<212> TYPE: DNA
<213> ORGANISM: Artificial Sequence
<220> FEATURE:
<223> OTHER INFORMATION: Description of Artificial Sequence:6-Mer primer

<400> SEQUENCE: 1 gactga                                                                   6

<210> SEQ ID NO 2
<211> LENGTH: 6
<212> TYPE: DNA
<213> ORGANISM: Artificial Sequence
<220> FEATURE:
<223> OTHER INFORMATION: Description of Artificial Sequence:6-Mer primer

<400> SEQUENCE: 2 gctctg                                                                   6

<210> SEQ ID NO 3
<211> LENGTH: 12
<212> TYPE: DNA
<213> ORGANISM: Artificial Sequence
<220> FEATURE:
<223> OTHER INFORMATION: Description of Artificial Sequence:DNA
      primer/template sequence

<400> SEQUENCE: 3
cgataggctc tg                                                           12

```
<210> SEQ ID NO 4
<211> LENGTH: 30
<212> TYPE: DNA
<213> ORGANISM: Artificial Sequence
<220> FEATURE:
<223> OTHER INFORMATION: Description of Artificial Sequence:DNA
      primer/template sequence

<400> SEQUENCE: 4
ttgtccacag ttcagtccca gagcctatcg                                    30

<210> SEQ ID NO 5
<211> LENGTH: 30
<212> TYPE: DNA
<213> ORGANISM: Artificial Sequence
<220> FEATURE:
<223> OTHER INFORMATION: Description of Artificial Sequence:
      6-mer/template

<400> SEQUENCE: 5
ttgtccacag ttcagtcaca gagcctatcg                                    30

<210> SEQ ID NO 6
<211> LENGTH: 14
<212> TYPE: DNA
<213> ORGANISM: Artificial Sequence
<220> FEATURE:
<223> OTHER INFORMATION: Description of Artificial Sequence:Single
      stranded polynucleotides

<400> SEQUENCE: 6
ctatccgatc catc                                                     14

<210> SEQ ID NO 7
<211> LENGTH: 56
<212> TYPE: DNA
<213> ORGANISM: Artificial Sequence
<220> FEATURE:
<223> OTHER INFORMATION: Description of Artificial Sequence:
      Single-stranded polynucleotides.

<400> SEQUENCE: 7
tacgctgtgg acaaatgttg agactgtttc gagactgaac ttgatggatc ggatag       56

<210> SEQ ID NO 8
<211> LENGTH: 56
<212> TYPE: DNA
<213> ORGANISM: Artificial Sequence
<220> FEATURE:
<223> OTHER INFORMATION: Description of Artificial Sequence:
      Single-stranded polynucleotides

<400> SEQUENCE: 8
ctatccgatc catcaagttc agtctcgaaa cagtctcaac atttgtccac agcgta       56
```